United States Patent [19]

Grate et al.

[11] Patent Number: 4,600,793

[45] Date of Patent: Jul. 15, 1986

[54] PROCESS FOR THE PREPARATION OF URETHANES

[75] Inventors: John H. Grate, Palo Alto; David R. Hamm, Mountain View; Donald H. Valentine, Santa Clara, all of Calif.

[73] Assignees: Catalytica Associates, Mountain View, Calif.; Haldor Topsoe A/S, Copenhagen, Denmark

[21] Appl. No.: 532,784

[22] Filed: Sep. 16, 1983

[51] Int. Cl.$^4$ .............. C07C 125/065; C07C 125/073; C07C 125/077

[52] U.S. Cl. ........................................ 560/25; 560/24; 560/27; 560/28; 560/29; 560/30; 560/32; 560/115; 560/157; 560/158; 560/163; 560/164

[58] Field of Search .................. 560/24, 25, 27, 28, 560/29, 30, 32, 115, 157, 158, 163, 164

[56] References Cited

U.S. PATENT DOCUMENTS

| | | | |
|---|---|---|---|
| 3,448,140 | 6/1969 | Gamlen et al. | 560/24 |
| 3,993,685 | 11/1976 | Zajacek et al. | 560/24 X |
| 4,297,501 | 10/1981 | Becker et al. | 560/24 |
| 4,474,978 | 10/1984 | Drent et al. | 560/24 |
| 4,491,670 | 1/1985 | Bhaduri et al. | 560/24 |

FOREIGN PATENT DOCUMENTS

| | | | |
|---|---|---|---|
| 0086281 | 8/1983 | European Pat. Off. | 560/24 |
| 55-007227 | 1/1980 | Japan | 560/24 |
| 55-102855 | 12/1980 | Japan | 560/24 |

*Primary Examiner*—Bernard Helfin
*Attorney, Agent, or Firm*—Robert J. Baran; John H. Grate

[57] ABSTRACT

A process for preparing urethanes by reacting a solution of a nitrogen-containing organic compound and a hydroxyl-containing organic compound with carbon monoxide in the presence of a halide-free ruthenium catalyst is disclosed. In the process of this invention, the rate of conversion and selectivity to urethane is increased by providing a primary amine in the reaction solution.

18 Claims, No Drawings

PROCESS FOR THE PREPARATION OF URETHANES

BACKGROUND OF THE INVENTION

1. Field of the Invention

This invention relates to a process for preparing urethanes by reacting a solution of a nitrogen-containing organic compound and a hydroxyl-containing organic compound with carbon monoxide in the presence of a halide-free ruthenium catalyst. In the process of this invention, the rate of conversion and selectivity to urethane is increased by providing a primary amine in the reaction solution.

2. Description of the Art

Isocyanates such as toluene di isocyanate (TDI) and 4,4'-diisocyanato diphenyl methane (MDI) are used commercially in the preparation of urethane polymers. The present commercial technology for the preparation of these isocyanates utilizes phosgene, which is costly, toxic, corrosive, and difficult to handle. It is thus understandable that a great deal of recent research has been directed toward different methods for preparing isocyanates, especially TDI and MDI.

Various patents have disclosed methods for carbonylating nitrogen-containing organic compounds, e.g. nitro compounds amines, azo-and azoxy compounds to either isocyanates or urethanes in the presence of a platinum group metal-containing catalyst; usually a palladium or rhodium-containing catalyst, and most often a palladium halide-containing catalyst. (The urethanes can be decomposed to yield the corresponding isocyanates.) Generally, a cocatalyst (promoter) or a coreactant has been utilized in combination with the aforementioned platinum group metal-containing catalysts; Lewis acids, Lewis bases, oxidizing agents, reducing agents, etc. have been used as cocatalysts or coreactants in the platinum group metal-catalyzed carbonylation of nitrogen-containing organic compounds. It is important to note that the vast majority of the research on the carbonylation of nitrogen-containing organic compounds has been directed to catalysis by rhodium or palladium-containing catalysts; especially palladium halide-containing catalysts. Therefore the cocatalysts or coreactants, that have been disclosed, have a demonstrable effect on the activity and selectivity of a palladium-containing catalyst; but the effect of such cocatalysts on the activity or selectivity of other platinum group metals or compounds is speculative.

Due to the complex nature of catalysis, it is often difficult to predict the effect of a known cocatalyst or coreactant on a catalyst having a different metal as the catalytically active moiety. Therefore, although U.S. Pat. No. 4,178,455 discloses that the reaction rate and yield (in a platinum group metal catalyzed process for preparing an aromatic urethane) is increased by a promoter consisting of a Lewis acid (e.g. metal halides, and especially iron chlorides); an organic primary amino compound, a urea compound, a biuret compound, an allophanate compound, or a mixture thereof; it is not obvious that such promoter is effective either in the absence of the Lewis acid or with a platinum group metal or platinum group metal compound other than palladium or palladium chloride. As a result, the effect of the promoter, disclosed in U.S. Pat. No. 4,178,455, on other catalyst metals can not be predicted with a reasonable degree of certainty.

It is known that palladium must be in the $Pd^{+2}$ oxidation state to catalyze the production of urethanes from nitro-aromatics; however, during the reaction $Pd^{+2}$ is converted to the inactive $Pd^{o}$ oxidation state. The nitro-aromatic can only slowly reoxidize the inactive $Pd^{o}$ to the active $Pd^{+2}$ oxidation state; therefore, an iron compound, or other similar Lewis acids are used as promoters. While not wishing to be bound by theory, it is believed that the palladium-catalyzed carbonylation of nitro aromatics is represented by the following equations, (wherein nitrobenzene and ethanol represent the reactants and $PdCl_2$ and $FeCl_2$ represent the palladium catalyst and cocatalyst, respectively).

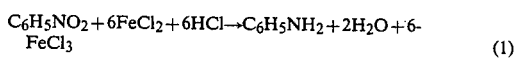

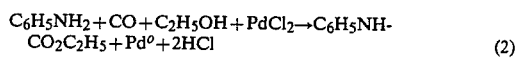

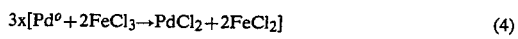

Net Reaction:
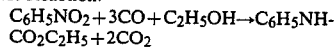

In this reaction scheme $Fe^{+2}$ reduces nitrobenzene to aniline and water, becoming oxidized to $Fe^{+3}$ (1). $Pd^{+2}$ converts aniline to urethane, becoming reduced to $Pd^{o}$ (2). The water and carbon monoxide are shifted to carbon dioxide in another process which reduces $Pd^{+2}$ to $Pd^{o}$ (3). $Pd^{o}$ is reoxidized by $Fe^{+3}$, regenerating $Pd^{+2}$ and $Fe^{+2}$ (4). The role of iron chlorides or similar Lewis Acids in the Pd-catalyzed carbonylation system may thus be defined as the catalysis of reoxidation of $Pd^{o}$ by nitroaromatic reduction to the amine. In view of the above, it may be understood, why the palladium catalyzed carbonylation of nitroaromatics requires an iron halide or a similar Lewis Acid as a promoter.

In the few references which suggest that ruthenium compounds are suitable catalysts for the carbonylation of nitrogen-containing organic compounds to the corresponding urethanes or isocyanates, the catalyst is either a ruthenium halide, or a halide-containing moiety is combined with the ruthenium compound to provide the active catalyst. For example, in U.S. Pat. Nos. 3,660,458; 4,134,880; and 4,186,269; the ruthenium compound that has demonstrated catalytic activity is ruthenium chloride. In U.S. Pat. Nos. 3,461,149 and 3,979,427 ruthenium-on-alumina is treated with halide-containing compounds, such as ferric chloride or 1,1,2-trichloro - 1,2,2,-trifluoroethane, to provide a heterogeneous catalyst.

Another example of a heterogeneous ruthenium catalyst for the preparation of aromatic isocyanates may be found in U.S. Pat. No. 3,737,445. This patent discloses a gas-phase process for reacting carbon monoxide with an aromatic nitro or nitroso compound to yield an aromatic isocyanate.

Ruthenium compounds have been utilized in the reduction of organic nitro compounds to the corresponding amines with mixtures of hyrogen and carbon monoxide. It was reported in U.S. Pat. No. 3,729,512 that the reduction of the organic nitro compound with carbon monoxide and ethanol, in the absence of $H_2$, resulted in a mixture of amine and a urethane. The patentee was not concerned with the preparation of a urethane product; therefore, there was no attempt to increase the selectivity above the approximately 22 percent, urethane, that was obtained.

SUMMARY OF THE INVENTION

It is, accordingly, one object of this invention to provide an improved process for converting a nitrogen-containing organic compound, selected from the group consisting of nitro, nitroso, azo and azoxy compounds into the corresponding urethane by reacting a solution, comprising a hydroxyl-containing organic compound and the nitrogen-containing organic compound, with carbon monoxide, in the presence of a ruthenium-containing catalyst. In the process of this invention, the rate of conversion of the nitrogen-containing organic compound and the selectivity of the conversion of said nitrogen-containing organic compound to the corresponding urethane is increased by (a) providing a primary amine in the solution of the hydroxyl-containing organic compound and the nitrogen-containing organic compound and (b) reacting the resulting solution with carbon monoxide in the presence of a halide-free ruthenium compound, at conditions sufficient to convert the nitrogen-containing organic compound to the corresponding urethane.

While not wishing to be bound by theory, it appears that, in the ruthenium catalyzed carbonylation of the above nitrogen-containing organic compound to the corresponding urethane, the nitrogen-containing organic compound must first be reduced to a primary amine which then undergoes oxidative carbonylation to the urethane. These reactions which are illustrated below (wherein [H] represents the ruthenium hydrogen carrier) must be effectively coupled to provide the desired selectivity to the urethane.

Oxidative carbonylation: 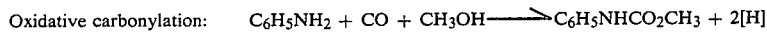

Reduction/hydrogenation: 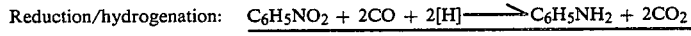

Net reaction: 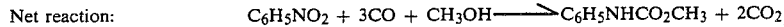

Thus the primary amine (illustrated by aniline) is an intermediate in the formation of urethane from the nitrogen-containing organic compound. It has been found that the halide-free ruthenium compounds used as catalysts in this invention are able to efficiently and rapidly reduce the nitrogen-containing organic compounds to the primary amine. The presence of iron chlorides or similar Lewis Acids is ineffective for increasing the activity of halide-free ruthenium catalysts.

In a carbonylation reaction wherein no primary amine is present, initially, the nitrogen-containing compound (e.g. nitrobenzene) can be reduced to the primary amine (aniline) by added hydrogen or hydrogen equivalents derived from water by the ruthenium-catalyzed water-gas shift reaction. It has been found that the reduction of the nitrogen-containing organic compound to a primary amine in the presence of hydrogen is rapid and provided that the molar ratio of hydrogen to the nitrogen-containing organic compound is less than 1, the remainder of the nitrogen-containing organic compound serves as the oxidant for the oxidative carbonylation of the primary amine to the urethane. Thus, decreasing the molar ratio of hydrogen to the nitrogen-containing organic compound provides urethane in greater selectivity. In the absence of hydrogen, water, or primary amine, the rate of the reaction is very slow as the hydrogen required to reduce the nitrogen containing organic compound to the primary amine intermediate must be derived by the relatively slow oxidation of alcohol. Moreover, the aldehydes which also result from the oxidation of alcohol, react with the primary amine to form unwanted condensation products.

The primary amine may also be provided by the in-situ decomposition of a urea or a biuret compound to the corresponding primary amine (s) and urethane in the reaction solution. It has been found that the primary amine substantially increases the rate of conversion of the nitrogen-containing organic compound to the corresponding urethane and provides a selectivity to urethane of 88 percent, or greater, at 100 percent conversion of the nitrogen-containing organic compound.

DETAILED DESCRIPTION OF THE INVENTION

The nitrogen-containing organic compound useful in the process of this invention will contain at least one non-cyclic group in which a nitrogen atom is directly attached to a single carbon atom and through a double bond to oxygen or another nitrogen atom. The nitrogen-containing organic compound is selected from the group consisting of nitro, nitroso, azo and azoxy compounds.

Examples of suitable nitrogen-containing organic compounds for use in the process of this invention are compounds represented by the general formulae:

      I

      II wherein $R_1$ and $R_2$ are radicals independently selected from the group consisting of $C_1$ to $C_{20}$ hydrocarbyl radicals and substituted derivatives therof, x is an integer of from 1 to 2, y is an integer of from 1 to 3, and z is an integer of from 0 to 1. The substituted hydrocarbyl radical may include hetero atoms selected from the group consisting of halogen, oxygen, sulfur, nitrogen and phosphorous atoms.

The nitrogen-containing compounds represented by formula 1 include nitro compounds (wherein x is 2) and nitroso compounds (wherein x is 1). Suitable nitro compounds are mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, tolyl, naphthyl, xylyl, chlorophenyl, chloronitrobenzenes, aminonitrobenzenes, carboalkoxyamino nitrobenzenes wherein the alkoxy group has up to 10 carbon atoms, dinitro compounds such as dinitrobenzene, alkyl and alkoxy dinitrobenzenes wherein the alkyl group contains up to 10 carbon atoms, aryl and aryloxy dinitrobenzenes, trinitro compounds such as trinitrobenzene, alkyl and alkoxytrinitrobenzenes, aryl and aryloxytrinitrobenzenes, the substituents being any of those already mentioned and chlorotrinitrobenzenes as well as similarly substituted mono and polynitro derivatives of the naphthalene, diphenyl, diphenylmethane, anthracene and phenanthrene series. Substituted or unsubstituted aliphatic nitro compounds such as nitromethane, nitrobutane, 2,2'-dimethyl nitrobutane, nitrocyclopentane, 3-methylnitrobutane, nitrooctadecane, 3-nitropropene-1, phenyl nitromethane, p-bromophenyl nitromethane, p-methoxy phenyl nitromethane, dinitroethane, dinitrohexane, dinitrocyclohexane, di-(nitrocyclohexyl)-methane are also suitable. The above nitro compounds may include more than one of the above substitutents (in addition to the nitro group (s) such as in nitroaminoalkylbenzenes, nitroalkylcarboalkoxyamino benzenes, etc. From this group of nitro compounds nitrobenzene, nitrotoluene, dinitrobenzene, dinitrotoluene, trinitrobenzene, trinitrotoluene, mononitronaphthalene, dinitronaphthalene, 4,4'-dinitrodiphenylmethane, nitrobutane, nitrocyclohexane, p-nitrophenylnitromethane, dinitrocyclohexane, dinitromethylcyclohexane, dinitrocyclohexylmethane, nitroaminotoluene and nitrocarboalkoxyaminotoluene are preferred and in particular aromatic nitro compounds especially 2,4-and 2,6-dinitrotoluenes, meta and para dinitrobenzenes, and 5-nitro-2-methyl-carboalkoxyamino-, 2-nitro-5-methyl-carboalkoxyamino-, and 3-nitro-2-methylcarboalkoxyamino benzenes.

Examples of suitable nitroso compounds are the aromatic nitroso compounds such as nitrosobenzene, nitrosotoluene, dinitrosobenzene, dinitrosotoluene and the aliphatic nitroso compounds such as nitrosobutane, nitrosocyclohexane and dinitrosomethylcyclohexane.

The nitrogen-containing compounds represented by Formula II include both azo compounds (wherein z is 0) and azoxy compounds (wherein z is 1). Suitable compounds represented by formula II include azobenzene, nitroazobenzene, chloroazobenzene, alkyl or aryl substituted azobenzene, azoxybenzene, nitroazoxybenzene, chloroazoxybenzene, etc.

The hydroxy-containing organic compound for use in the process of this invention include compounds represented by the general formula $$R_1(OH)_y \qquad \text{III}$$

wherein $R_1$ and y are defined above.

Hydroxy compounds suitable for use in the process of the present invention may be, for example, mono-or polyhydric alcohols containing primary, secondary or tertiary hydroxyl groups as well as mono-and polyhydric phenols. Mixtures of these hydroxy compounds may also be used. The alcohols may be aliphatic or aromatic and may bear other substituents in addition to hydroxyl groups but the substituents should (except as hereinafter described) preferably be non-reactive to carbon monoxide under the reaction conditions. Especially suitable compounds are phenol and monohydric alcohols such as methyl, ethyl, n- and sec-propyl, n-, iso, sec-and tert butyl, amyl, hexyl, lauryl, cetyl, benzyl, chlorobenzyl and methoxybenzyl alcohols as well as diols such as ethylene glycol, diethylene glycol, propylene glycol and dipropylene glycol, triols such as glycerol, trimethylol propane, hexanetriol, tetrols such as pentaerythritol and the ethers of such polyols providing that at least one hydroxyl group remains unetherified. The etherifying group in such ether alcohols normally contains up to 10 carbon atoms and is preferably an alkyl, cycloalkyl or aralkyl group which may be substituted with, for example, a halogen or an alkyl group.

The most preferred hydroxyl-containing organic compound for use in the process of this invention is methyl alcohol or a similar lower alkanol, e.g. a $C_1$ to $C_5$ alcohol.

The process of this invention includes the use of any mixture of nitro compounds, nitroso compounds, azo or azoxy compounds with any mixture of hydroxy compounds and also the use of compounds containing both functions, i.e. hydroxynitro compounds, hydroxynitroso compounds, hydroxyazo and hydroxyazoxy compounds such as 2-hydroxynitroethane, 2-hydroxynitrosoethane, nitrophenols, nitronaphthols, nitrosophenols, nitrosonaphthols hydroxyazobenzenes and hydroxyazoxybenzenes. Mixtures of these nitrogen-containing compounds may also be used.

This process of the invention has been found to proceed most smoothly to give the highest yields when employing nitro compounds. It is accordingly preferred to use nitro compounds rather than nitroso, azo or azoxy compounds.

The primary amine compound utilized in the process of this invention may be selected from the group consisting of compounds represented by the general formula:

$$R_1(NH_2)_y \qquad \text{IV}$$

wherein $R_1$ and y are as defined above. Examples of such primary amines include methylamine, ethylamine, butylamine, hexylamine, ethylenediamine, propylenediamine, butylenediamine, cyclohexylamine, cyclohexyldiamine, aniline, p-toluidine, o-, m-and p-diaminobenzenes, amino-methylcarbanilic acid esters, especially the 5-amino-2 methyl-, 2-amino-5-methyl-, and 3-amino-2-methyl carboalkoxyaminobenzenes, wherein said alkoxy group has up to 10 carbon atoms, o-, m- and p-nitroanilines, nitroaminotoluenes, especially those designated above, o-and p-phenylenediamine, benzylamine, o-amino-p-xylene, 1-aminophthalene, 2,4-and 2,6-diaminotoluenes, 4,4'-diaminodibenzyl, bis (4-aminophenyl) thioether, bis (4-aminophenyl) sulfone, 2,4,6-triaminotoluene, O-, m-and p-chloranilines p-bromoaniline, 1-fluoro-2,4-diaminobenzene, 2,-4-diaminophenetole, o,-m- and p-aminoanisoles, ethyl p-aminobenzoate, 3-aminophthalic anhydride, etc. These amino compounds may be used alone or in conbination.

Among the above-enumerated amino compounds, those which can be derived from the starting nitro compound are preferred. For example, when nitrobenzene is used as the starting aromatic nitro compound, aniline is preferred. Similarly, 2-amino-4-nitrotoluene, 4-amino-2-nitrotoluene, and 2,4-diaminotoluene are preferably used when the starting aromatic nitro compound is 2,4-dinitrotoluene, while 2-amino-6-nitrotoluene, and 2,6-diaminotoluene are preferably used when the starting aromatic nitro compound is 2,6-dinitrotoluene.

The primary amine compound can be provided by the in-situ decomposition of the corresponding urea or biuret as represented by compounds having the general formulae:

$$R_1NH-\underset{\underset{O}{\|}}{C}-NHR_1$$

-continued and

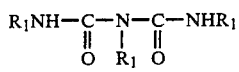

respectively, wherein $R_1$ is as defined above. Of course, since the above urea and biuret will comprise more than one radical, $R_1$ may represent different radicals in the same compound. That is non-symmetrical ureas and biurets, e.g.

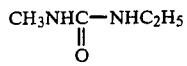

are within the scope of the invention.

The catalyst utilized in the process of this invention comprises a halide-free ruthenium compound. Unlike other platinum group metal-containing catalysts for the carbonylation of nitrogen-containing organic compounds, the presence of halide in ruthenium catalysts, either as the anion of a ruthenium salt or in a Lewis acid decreases the activity of the ruthenium catalyst. Thus the ruthenium compound may be selected from ruthenium salts, e.g. the nitrate, sulfate, acetate, formate, carbonate, etc. and ruthenium complexes (especially ruthenium carbonyl complexes) including ligands capable of coordinating with the ruthenium atom. The complex may include one or more ruthenium atoms and suitable ligands may include carbon-carbon unsaturated groups as in ethylene, isobutylene, cyclohexene, cyclopentadiene, norbornadiene, cyclooctatetraene. Other suitable ligands include acetylacetonate (acac), hydrogen atoms, carbon monoxide, nitric oxide, alkylradicals, alkyl or aryl nitriles or isonitriles, nitrogen-containing heterocyclic compounds such as pyridine, 2,2'-bipyridine (bipy), piperidine, and organo phosphines, arsines or stibines.

The ruthenium catalyst is preferably utilized as a homogeneous catalyst and therefore one criteria for the selection of the ruthenium compound is its solubility under the conditions of reaction in the mixture of the nitrogen-containing organic compound, the hydroxyl-containing organic compound and the primary amino compound. The ruthenium compound is also selected with a view toward the catalytic activity of the compound. Thus the organo phosphines are useful ligands for incorporation into the ruthenium catalyst utilized in the process of the instant invention.

Suitable organophosphines include compounds represented by the following formula $(R_3)(R_4)P(R_5)$   V wherein $R_3$, $R_4$ and $R_5$ are radicals independently selected from the group consisting of hydrogen, hydrocarbyl, and substituted derivatives of hydrocarbyl radicals, and wherein the substituted hydrocarbyl radicals may include heteroatoms selected from the group consisting of halogen, oxygen, sulfur, nitrogen and phosphorous atoms, Preferably the above hydrocarbyl radicals will comprise from 1 to about 20 carbon atoms, e.g. from about 1 to about 10 carbon atoms. Suitable radicals include methyl, ethyl, n-propyl, isopropyl, butyl, 2-chlorobutyl, n-propoxy, 2-nitro pentyl, phenyl, fluorophenyl, o,m, and p-methylphenyl, etc.

Examples of suitable organophosphines include triphenylphosphine, methyldiphenylphosphine, tris o-chlorophenylphosphine, tri-n-propylphosphine, tris-p-methoxybenzylphosphine, etc.

Examples of ruthenium compounds which are suitable as catalysts for the process of this invention include:

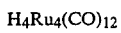

Ruthenium acetylacetonate

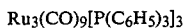

No particular limitation is placed on the amount of primary amine used. However, it is preferably used in an amount equal to from 0.1 to 100 moles per gm-atom of nitrogen in the nitrogen-containing organic compound. The process of the invention may be carried out in the absence of solvent but the use of a solvent is not precluded. Suitable solvents include, for example, aromatic solvents such as benzene, toluene, xylene, etc.; nitriles such as acetonitrile, benzonitrile, etc.; sulfones such as sulfolane, etc.; halogenated aliphatic hydrocarbons such as 1,1,2-trichloro-1,2,2,-trifluoroethane, etc.; halogenated aromatic hydrocarbons such as monochlorobenzene, dichlorobenzene, trichlorobenzene, etc.; ketones; esters; and other solvents such as tetrahydrofuran, 1,4-dioxane, 1,2-dimethoxyethane, etc.

In carrying out the process of the invention, the hydroxyl-containing organic compound and carbon monoxide may be used in amounts equal to at least 1 mole per gm-atom of nitrogen in the nitrogen-containing compound. Preferably the hydroxyl-containing organic compound is used in excess and functions as a solvent as well as reactant.

The amount of the ruthenium compound used as the catalyst may vary widely according to the type therof and other reaction conditions. However, on a weight basis, the amount of catalyst is generally in the range of from $1 \times 10^{-5}$ to 1 part, and preferably from $1 \times 10^{-4}$ to $5 \times 10^{-1}$ part, per gram-atom of nitrogen in the starting nitrogen-containing organic compound when expressed in terms of its metallic component.

The reaction temperature is generally held in the range of 80° to 230° C., and preferably from 130° to 200° C.

The reaction pressure, or the initial carbon monoxide pressure, is generally in the range of from 10 to 1,000 kg/cm²G, and preferably from 30 to 500 kg/cm²G.

The reaction time depends on the nature and amount of the nitrogen-containing organic compound used, the reaction temperature, the reaction pressure, the type and amount of catalyst used, the type of reactor employed, and the like, but is generally in the range of from 5 minutes to 6 hours. After completion of the reaction, the reaction mixture is cooled and the gas is discharged from the reactor. Then, the reaction mixture is subjected to any conventional procedure including filtration, distillation, or other suitable separation steps, whereby the resulting urethane is separated from any unreacted materials, any by-products, the solvent, the catalyst, and the like.

The urethanes prepared by the process of the invention have wide applications in the manufacture of agricultural chemicals, isocyanates, and polyurethanes.

This invention is more fully illustrated by the following examples. However, they are not to be construed to limit the scope of the invention.

In each of the following examples, the reaction was conducted in batch mode in a 300 ml stainless steel autoclave reactor equipped with a stirring mechanism which provides constant disperstion of the gas through the liquid solution. Heating of the reaction is provided by a jacket-type furnace controlled by a proportioning controller. The autoclave is equipped with a high pressure sampling system for removal of small samples of the reaction solution during the reaction in order to monitor the reaction progress and determine reaction rates. Reaction samples were analyzed by gas chromatography.

EXAMPLE 1

75 ml of solution containing 6.16 g (0.050 mole) of nitrobenzene, 4.66 g (0.050 mole) of aniline, and 2.68 g of t-butylbenzene (internal standard for gas chromatographic analyses) in methanol and 0.128 g $Ru_3(CO)_{12}$ (600 microgramatoms of ruthenium) were placed in the reactor vessel. The gas volume in the vessel was replaced with carbon monoxide and then pressurized with carbon monoxide to 1000 psig at ambient temperature. The reactor contents were then heated to 160° C. The initial turnover frequency at this temperature was determined to be 0.36 moles nitrobenzene converted per gramatom ruthenium per minute. After 4.5 hours at 160° C., nitrobenzene conversion was complete and the solution contained 0.037 mole methyl-N-phenyl carbamate (74% selectivity based on nitrobenzene), 0.059 mole aniline (18% selectivity based on nitrobenzene), and 0.003 mole total of formylidene aniline plus N-methyl aniline (6% selectivity).

EXAMPLE 2

The procedure is the same as for Example 1 with the exception that 12.31 g (0.10 mole) nitrobenzene is introduced to the reaction. After 8.5 hours at 160° C., nitrobenzene conversion is complete and the solution contains 0.085 moles carbamate (85% selectivity based on nitrobenzene) and 0.062 mole aniline (12% selectivity based on nitrobenzene).

A comparison of Examples 1 and 2 indicates that increasing the amount of nitrobenzene converted in the reaction increases the selectivity to the desired urethane product.

COMPARATIVE EXAMPLE 2

The procedure was the same as for Example 2 with the exception that no aniline was introduced to the reaction. Complete nitrobenzene conversion required 26 hours at 160° C. Selectivities based on nitrobenzene were 38 percent to phenyl urethane, 32 percent to aniline, 12 percent total to formylidene aniline and N-methyl aniline. The balance was converted to higher molecular weight products derived from aniline.

It is thus clear that the rate of conversion of nitrobenzene and the selectivity of the conversion of nitrobenzene to the corresponding urethane is increased by providing the corresponding primary amine in the reaction solution even when the amount of nitrobenzene converted in the reaction is also increased.

EXAMPLES 3–5

For these examples, the procedure is the same as for Example 1 with the exception that various halide-free ruthenium compounds and various ruthenium catalyst loadings are used. The results obtained are given in Table 1.

TABLE 1

| Example | Ruthenium Compound | Catalyst Loading (microgram-atom Ru) | Initial Turnover Frequency at 160° C. ($min^{-1}$) | Selectivity to Phenyl urethane at 100% Nitrobenzene Conversion |
|---|---|---|---|---|
| 3 | $Ru_3(CO)_{12}$ | 60 | 0.65 | 74 |
| 4 | $H_4Ru_4(CO)_{12}$ | 600 | 0.40 | 78 |
| 5 | $(Ru(CO)_2(HCO_2))_n$ n is an integer | 200 | 0.48 | 80 |
| 6 | $Ru_3(CO)_9(P(C_6H_5)_3)_3$ | 600 | 0.36 | 72 |
| 7 | $(Ru(CO)_2(HCO_2)(P(c-C_6H_{11})_3))_2$ | 200 | 0.46 | 80 |

COMPARATIVE EXAMPLE I

The procedure is the same as for Example 1 with the exception that no aniline is introduced to the reaction. Additional methanol was added so that the total initial solution volume is again 75 ml. The initial turnover frequency at 160° C. is 0.10 moles nitrobenzene converted per gram-atom ruthenium per minute. Complete nitrobenzene conversion requires 12 hours at 160° C. Selectivities based on nitrobenzene are 24 percent to phenyl urethane (methyl-N-phenyl carbamate), 58 percent to aniline, and 11 percent total to formylidene aniline plus N-methyl aniline. The balance is converted to higher molecular weight products derived from aniline.

It is thus clear that the rate of conversion of nitrobenzene and the selectivity of the conversion of nitrobenzene to the corresponding urethane is increased by providing the corresponding primary amine in the reaction solution.

EXAMPLE 8

The procedure is the same as for Example 1 with the exception that 0.24 g tris (acetylacetonate) ruthenium (600 ug-atoms ruthenium) is used as catalyst precursor. After an initial induction period, the rate of nitrobenzene conversion reaches 0.47 moles nitrobenzehe per g-atom ruthenium per minute. After 6 hours at 160° C., nitrobenzene conversion is complete. Selectivities based on nitrobenzene are 65 percent to phenylurethane, 26 percent to aniline, and 9 percent to formylidene aniline. This example demonstrates that ruthenium compounds, that do not contain carbon monoxide ligands, are useful as catalysts in the process of this invention; however, an induction period may be necessary to convert such ruthenium compounds to the carbonyl.

EXAMPLE 9

The procedure is the same as for Example 1 with the exception that 0.13 g ruthenium trichloride (630 ug-atoms ruthenium) is introduced as catalyst. After 5 hours at 160° C., nitrobenzene conversion is 7 percent with 100 percent selectivity to aniline. Complete nitrobenzene conversion requires 24 hours and gives 38 percent selectivity to phenyl urethane and 21 percent selectivity to aniline. The balance is converted to higher molecular weight materials. This example demonstrates that ruthenium halides, are ineffective as catalysts in the process of this invention.

EXAMPLE 10

The procedure is the same as for Example 1 with the exception that 0.154 g [Ru(CO)$_3$Cl$_2$]$_2$ (600 ug-atoms ruthenium) is introduced as catalyst. After 5 hours at 160° C., nitrobenzene conversion was 8 percent with 100 percent selectivity to aniline. This example demonstrates ruthenium carbonyl compounds containing halide anions are also ineffective as catalysts for the process of this invention.

EXAMPLE 11

The procedure is the same as for Example 1 with the exception that both 0.128 g Ru$_3$(CO)$_{12}$ and 0.126 g RuCl$_3$ are introduced to the reaction. After 5 hours of reaction at 160° C., nitrobenzene conversion is 40 percent. Selectivity to phenyl urethane is 47 percent. Selectivity to aniline is 53 percent. This example demonstrates that halide salts, even ruthenium halides, can adversely affect the conversion and selectivity of the otherwise effective catalyst of Example 1.

EXAMPLE 12

The procedure is the same as for Example 1 with the exception that both 0.043 g Ru$_3$(CO)$_{12}$ and 0.036 g PdCl$_2$ are introduced to the reaction. After 5 hours reaction at 160° C., nitrobenzene conversion is 10 percent. Selectivity to phenyl urethane is 5 percent. Selectivity to aniline is 95 percent. This example demonstrates the difference between the prior art palladium catalyst and the catalysts used in the process of this invention. In particular, it would appear that the mode of action of the ruthenium catalysts described herein and the prior art palladium catalyst differ significantly in that the individual catalytic effectiveness of each is hindered by combination with the other.

EXAMPLE 13

The procedure is the same as for Example 1 with the exception that the initial carbon monoxide pressure at ambient tmeperature is 500 psig. Nitrobenzene conversion was complete after 6 hours at 160° C. and selectivity to phenyl urethane is 68 percent. This example demonstrates that a lower partial pressure of carbon monoxide may be used, in the process of this invention, with only a slight decrease in rate of reaction and selectivity to urethane.

EXAMPLE 14

The procedure was the same as for Example 1 with the exception that 5.36 g (0.050 mole) of p-toluidine was used instead of aniline. After 3 hours at 160° C., nitrobenzene conversion was complete and the solution contained 0.013 mole methyl-N-phenyl carbamate, 0.031 mole methyl-N-(tolyl) carbamate, 0.037 mole aniline and 0.019 mole p-toluidine. This example shows that when the primary amine does not correspond to the nitro compound, mixtures of urethanes may be obtained.

EXAMPLE 15

The procedure is the same as for Example 1 with the exception that 6.86 g p-nitrotoluene and 5.36 g p-toluidine are used as the nitroaromatic and arylamine. Nitrotoluene conversion is 100 percent after 3 hours at 160° C. Selectivity to methyl N-p-tolylcarbamate is 88 percent. Selectivity to p-toluidine is 10 percent. This example demonstrates that certain primary amines are more efficient in increasing the rate of reaction than others. For example, substituents such as a p-CH$_3$, having a $\sigma$p of $-0.17$, or substituents having a more negative Hammet $\sigma$ value, increase the rate of conversion of the nitroaromatic compound.

EXAMPLE 16

6.16 g (0.050 mole) nitrobenzene and 10.6 g (0.050 mole) N,N'-diphenyl urea were reacted in methanol by the procedure given in Example 1. The catalyst was 0.126 g (200 micromoles) of [bis(1,2-diphenylphosphino)benzene] ruthenium tricarbonyl. As the reaction contents were heated to 160° C. most of the N,N'-diphenyl urea was converted to equal parts aniline and phenyl urethane. The rate of nitrobenzene conversion at 160° C. reached 0.86 moles nitrobenzene converted per mole ruthenium per minute. After 5 hours at 160° C. nitrobenzene conversion was 100 percent and the solution contained 0.092 moles phenyl urethane and 0.048 moles aniline. This example demonstrates that a urea, which decomposes to provide a primary amine, i.e. aniline, in-situ, also increases the rate of conversion of nitrobenzene, and the selectivity of the conversion of nitrobenzene to the urethane.

EXAMPLE 17

12.3 g (0.100 mole nitrobenzene) in 75 ml of methanolic solution and 0.128 g Ru$_3$(CO)$_{12}$ (600 microgram-atoms ruthenium) were placed in the reactor vessel. The gas volume in the vessel was replaced with carbon monoxide and then pressurized at ambient temperature with 920 psig carbon monoxide and 80 psig hydrogen (approximately 0.05 mole hydrogen). The reactor contents were then heated to 160° C. Initially, aniline was produced from nitrobenzene in 100 percent selectivity. After approximately 0.030 moles aniline had been produced, phenyl urethane production also began. After a total of 7.5 hours at 160° C., nitrobenzene conversion was complete and the solution contained 0.060 moles aniline and 0.034 moles phenyl urethane. This example demonstrates that the primary amine may be provided by reduction of the nitrogen-containing organic compound, e.g. nitrobenzene, in-situ. Note that, once the added hydrogen is utilized to reduce the nitrobenzene to aniline, the selectivity of the conversion of the remaining nitrobenzene to the urethane is greater than 50 percent.

EXAMPLE 18

12.3 g (0.100 mole) nitrobenzene and 0.90 g (0.050 mole) water in 75 ml methanolic solution and 0.128 g Ru$_3$(Co)$_{12}$ (600 microgram-atoms ruthenium)were reacted under carbon monoxide as described in Example 1. When the reaction solution reached 160° C., 0.030 moles of aniline were present and phenyl urethane production began. After 6 hours at 160' C., nitrobenzene conversion was complete and the solution contained 0.061 moles aniline and 0.034 moles phenyl urethane. This example demonstrates that water can be utilized to provide hydrogen to reduce the nitrogen-containing organic compound (nitrobenzene) to the primary amine (aniline), in-situ. Again, as in Example 14, once substantially all of the hydrogen equivalents generated by the water-gas shift reaction are utilized to reduce nitrobenzene to aniline, the selectivity of the conversion of the remaining nitrobenzene to the urethane is greater than 50 percent.

While particular embodiments of the invention have been described, it will be understood, of course, that the invention is not limited thereto since many obvious modifications can be made and it is intended to include within this invention any such modifications as will fall within the scope of the appended claims.

Having now described the invention, what is claimed is:

1. A process for converting a nitrogen-containing organic compound, selected from the group consisting of nitro, nitroso, azo, and azoxy compounds, into the corresponding urethane, by reacting a solution comprising said nitrogen-containing organic compound and a hydroxyl-containing organic compound with carbon monoxide, which comprises the steps of:
   (a) providing a primary amine in said solution, and
   (b) contacting the solution of step (a) with carbon monoxide, in the presence of a catalyst comprising a halide-free ruthenium compound, at conditions sufficient to convert said nitrogen-containing organic compound into the said corresponding urethane.

2. The process of claim 1 wherein said nitrogen-containing organic compound is a nitro compound.

3. The process of claim 2 wherein said nitro compound is an aromatic nitro compound.

4. The process of claim 3 wherein said primary amine is an aromatic amine.

5. The process of claim 4 wherein said ruthenium compound comprises a phosphine ligand.

6. The process of claim 1 wherein said primary amine is provided by reduction of said nitrogen-containing compound with hydrogen in said solution.

7. The process of claim 1 wherein said primary amine is provided by reduction of said nitrogen-containing compound with hydrogen equivalents derived from the ruthenium-catalyzed water-gas shift reaction.

8. The process of claim 3 wherein said aromatic nitrocompound is selected from the group consisting of nitrobenzene, nitroanisole, dinitrotoluene, nitromesitylene, bis (4-nitrophenyl) methane, nitoaminotoluene and nitrocarboalkoxyaminotoluene.

9. The process of claim 8 wherein said amine is selected from the group consisting of p-toluidine, aniline, diaminotoluene bis (4-aminophenyl) methane, aminonitrotoluene, and aminomethylcarboalkoxybenzene.

10. The process of claim 1 wherein said amine is provided by decomposing a urea or biuret in-situ.

11. A procoss for converting a nitro-containing organic compound into the corresponding urethane, by reacting a solution comprising said nitro-containing organic compound and a lower alkanol with carbon monoxide, which comprises the steps of:
   (a) providing a primary amine to said solution,
   (b) contacting the solution of step (a) with carbon monoxide, in the presence of a catalyst comprising a halide-free ruthenium carbonyl compound, at a temperature of a least about 130° C. and a carbon monoxide pressure of at least about 200 psig to convert said nitro-containing organic compound to said corresponding urethane, and
   (c) recovering said urethane at a selectivity of at least 80 percent based on said nitro-containing organic compound reacted.

12. The process of claim 11 wherein said nitro-containing organic compound is an aromatic nitro compound and said primary amine is the corresponding aromatic amine.

13. The process of claim 12 wherein said aromatic nitro compound is selected from the group consisting of nitrobenzene, nitroanisole, dinitrotoluene, nitromesitylene, bis (4-nitrophenyl) methane, nitroaminotoluene and nitrocarboalkoxyaminotoluene.

14. The process of claim 12 wherein said ruthenium carbonyl compound comprises a phosphine ligand.

15. The process of claim 14 wherein said phosphine is an aryl phosphine.

16. The process of claim 14 wherein said phosphine is triphenylphosphine.

17. The process of claim 1 wherein said ruthenium catalyst is utilized as a homogeneous catalyst.

18. The process of claim 11 wherein halide-free ruthenium carbonyl compound is utilized as a homogeneous catalyst.

* * * * *